(12) United States Patent
Soma (10) Patent No.: US 9,585,592 B2
(45) Date of Patent: Mar. 7, 2017

(54) INFORMATION PROCESSING APPARATUS, PROGRAM, AND BIOSIGNAL MEASUREMENT SET

(71) Applicant: Sony Corporation, Tokyo (JP)

(72) Inventor: Haruhiko Soma, Tokyo (JP)

(73) Assignee: SONY CORPORATION, Tokyo (JP)

( * ) Notice: Subject to any disclaimer, the term of this patent is extended or adjusted under 35 U.S.C. 154(b) by 717 days.

(21) Appl. No.: 13/947,757

(22) Filed: Jul. 22, 2013

(65) Prior Publication Data

US 2014/0036055 A1 Feb. 6, 2014

(30) Foreign Application Priority Data

Aug. 3, 2012 (JP) ................. 2012-173357

(51) Int. Cl.
*H04N 9/47* (2006.01)
*A61B 5/0478* (2006.01)
*A61B 5/00* (2006.01)

(52) U.S. Cl.
CPC ............ *A61B 5/0478* (2013.01); *A61B 5/684* (2013.01)

(58) Field of Classification Search
USPC .................................................... 348/77, 80
See application file for complete search history.

(56) References Cited

U.S. PATENT DOCUMENTS

| 2008/0188763 A1* | 8/2008 | John | A61B 5/0452 600/516 |
| 2010/0049037 A1* | 2/2010 | Pinter | A61B 5/0408 600/425 |
| 2012/0093385 A1* | 4/2012 | Yokosawa | A61B 5/0037 382/131 |

FOREIGN PATENT DOCUMENTS

| JP | 2003-159225 | 3/2003 |
| JP | 2006-122086 | 5/2006 |

* cited by examiner

*Primary Examiner* — Nigar Chowdhury
(74) *Attorney, Agent, or Firm* — Chip Law Group (57) ABSTRACT

An information processing apparatus includes a retaining unit, an image acquisition unit, an image processor, a comparator, and an image generator. The retaining unit is configured to retain a defined attachment position being an attachment position of a biological detection sensor with respect to a body site of a user, the defined attachment position being defined in advance. The image acquisition unit is configured to acquire a capture image captured by an imaging unit. The image processor is configured to extract, from the capture image, a body shape of the user. The comparator is configured to compare the body shape with the defined attachment position. The image generator is configured to generate, based on a comparison result by the comparator, a display image to be displayed on a display unit.

11 Claims, 7 Drawing Sheets

INFORMATION PROCESSING APPARATUS, PROGRAM, AND BIOSIGNAL MEASUREMENT SET

CROSS REFERENCES TO RELATED APPLICATIONS

The present application claims priority to Japanese Priority Patent Application JP 2012-173357 filed in the Japan Patent Office on Aug. 3, 2012, the entire content of which is hereby incorporated by reference.

BACKGROUND

The present disclosure relates to an information processing apparatus, a program, and a biosignal measurement set that pertain to biosignal measurement carried out with a biosignal measurement sensor attached to a body of a user.

In medical home monitoring, a patient brings an apparatus back home and operates the apparatus himself or herself to measure a biosignal, and a doctor makes a diagnosis based on a measurement result thereof. However, a patient with no expertise who is unfamiliar with the apparatus may perform attachment of sensors and operations of the apparatus. As a result, in some cases, correct attachment of the sensors is not performed and an accurate diagnosis is not made based on the obtained measurement value.

Regarding an attachment support method for a sensor, for example, Japanese Patent Application Laid-open No. 2003-159225 (hereinafter, referred to as Patent Document 1) discloses an electrode wire retainer for an electroencephalographic measurement apparatus that enables easy recognition of attachment positions by an electrode holder on which a head is drawn. Further, Japanese Patent Application Laid-open No. 2006-122086 (hereinafter, referred to as Patent Document 2) discloses a head attachment support method for an optical topography (registered trademark) that makes a sound announcement when a sensor approaches an optimal attachment position.

SUMMARY

However, in the method described in Patent Document 1, it is difficult for the user to grasp an accurate attachment position because the head shape varies in users. Further, in the method of Patent Document 2, it is difficult for the user to rapidly attach the sensor at an appropriate attachment position. In addition, even by any method, it is difficult to determine whether or not the sensor is appropriately attached before measurement is carried out.

In view of the above-mentioned circumstances, it is desirable to provide an information processing apparatus, a program, and a biosignal measurement set that enable a user to appropriately attach a biological detection sensor to a living body of the user.

According to an embodiment of the present disclosure, there is provided an information processing apparatus including a retaining unit, an image acquisition unit, an image processor, a comparator, and an image generator.

The retaining unit is configured to retain a defined attachment position being an attachment position of a biological detection sensor with respect to a body site of a user, the defined attachment position being defined in advance.

The image acquisition unit is configured to acquire a capture image captured by an imaging unit.

The image processor is configured to extract, from the capture image, a body shape of the user.

The comparator is configured to compare the body shape with the defined attachment position.

The image generator is configured to generate, based on a comparison result by the comparator, a display image to be displayed on a display unit.

With this configuration, corresponding to the body shape of the user included in the capture image captured by the imaging unit, an image to which the defined attachment position is reflected is displayed on the display unit as the display image. Therefore, irrespective of differences in the body shape among the users and a relative position relationship between the user and the imaging unit, the user can grasp a relationship between the body shape of the user and the defined attachment position included in the capture image.

The image generator may be configured to generate the display image by overlapping the capture image with a marker located at a position on the capture image, the position corresponding to the defined attachment position.

With this configuration, the user can grasp the attachment position of the biological detection sensor, referring to the marker displayed in the display image.

The image processor may be configured to further detect, from the capture image, a detected attachment position being an attachment position of a biological detection sensor.

The comparator may be configured to further compare the defined attachment position with the detected attachment position.

With this configuration, the user can grasp a position relationship between a position at which the biological detection sensor is attached to the user (detected attachment position) and a position at which the biological detection sensor is to be normally attached (defined attachment position), by referring to the display image.

The image generator may be configured to generate, when the defined attachment position is different from the detected attachment position, the display image by overlapping the capture image with a marker located at a position on the capture image, the position corresponding to the defined attachment position different from the detected attachment position.

With this configuration, the user can grasp the fact that the position at which the biological detection sensor is attached to the user (detected attachment position) and the position at which the biological detection sensor is to be normally attached (defined attachment position) are different from each other, owing to the marker displayed in the display image. In addition, the user can grasp the normal attachment position for the different biological detection sensor owing to the marker displayed at a position corresponding to the defined attachment position on the display image.

The information processing apparatus further includes a sensor determination unit configured to determine an attachment state of the biological detection sensor.

The image generator may be configured to further generate the display image based on a determination result of the sensor determination unit.

With this configuration, a determination result of the attachment state of the biological detection sensor by the sensor determination unit is reflected to the display image. Therefore, the user can grasp whether or not the attachment state of the biological detection sensor attached to the user is appropriate.

The image generator may be configured to generate, when the attachment state is inappropriate, the display image by overlapping the capture image with a marker located at a position on the capture image, the position corresponding to the defined attachment position of the biological detection sensor the attachment state of which is inappropriate.

With this configuration, the user can grasp the biological detection sensor in which an attachment target is inappropriate (contact with body surface is insufficient, for example) owing to the marker displayed in the display image, and can perform a countermeasure such as re-attachment or the like of the biological detection sensor.

The biological detection sensor may include an electroencephalographic electrode.

The sensor determination unit may be configured to determine the attachment state based on contact resistance of the electroencephalographic electrode.

Whether or not the electroencephalographic electrode is held in firm contact with the scalp of the user is generally checked by measurement of contact resistance between the electroencephalographic electrode and the scalp before brain waves are measured in electroencephalographic measurement. That is because the contact resistance significantly increases if contact with the electroencephalographic electrode is insufficient. Therefore, with this configuration, the sensor determination unit can determine the attachment state of the electroencephalographic electrode based on the contact resistance.

According to another embodiment of the present disclosure, there is provided a program including a retaining unit, an image acquisition unit, an image processor, a comparator, and an image generator.

The retaining unit is configured to retain a defined attachment position being an attachment position of a biological detection sensor with respect to a body site of a user, the defined attachment position being defined in advance.

The image acquisition unit is configured to acquire a capture image captured by an imaging unit.

The image processor is configured to extract, from the capture image, a body shape of the user.

The comparator is configured to compare the body shape with the defined attachment position.

The image generator is configured to generate, based on a comparison result by the comparator, a display image to be displayed on a display unit.

According to still another embodiment of the present disclosure, there is provided a biosignal measurement set including a biosignal measurement apparatus and an information processing apparatus.

The biosignal measurement apparatus includes a biological detection sensor configured to detect a biosignal in a body of a user.

The information processing apparatus includes a retaining unit configured to retain a defined attachment position being an attachment position of the biological detection sensor to a body site of a user, the defined attachment position being defined in advance, an image acquisition unit configured to acquire a capture image captured by an imaging unit, an image processor configured to extract, from the capture image, a body shape of the user, a comparator configured to compare the body shape with the defined attachment position, and an image generator configured to generate, based on a comparison result by the comparator, a display image to be displayed on a display unit.

As mentioned above, according to the embodiments of present disclosure, it is possible to provide an information processing apparatus, a program, and a biosignal measurement set that enable a user to appropriately attach a biological detection sensor to a living body of the user.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

A biosignal measurement set according to an embodiment of the present disclosure will be described.

[Configuration of Biosignal Measurement Set]

Figure 1:
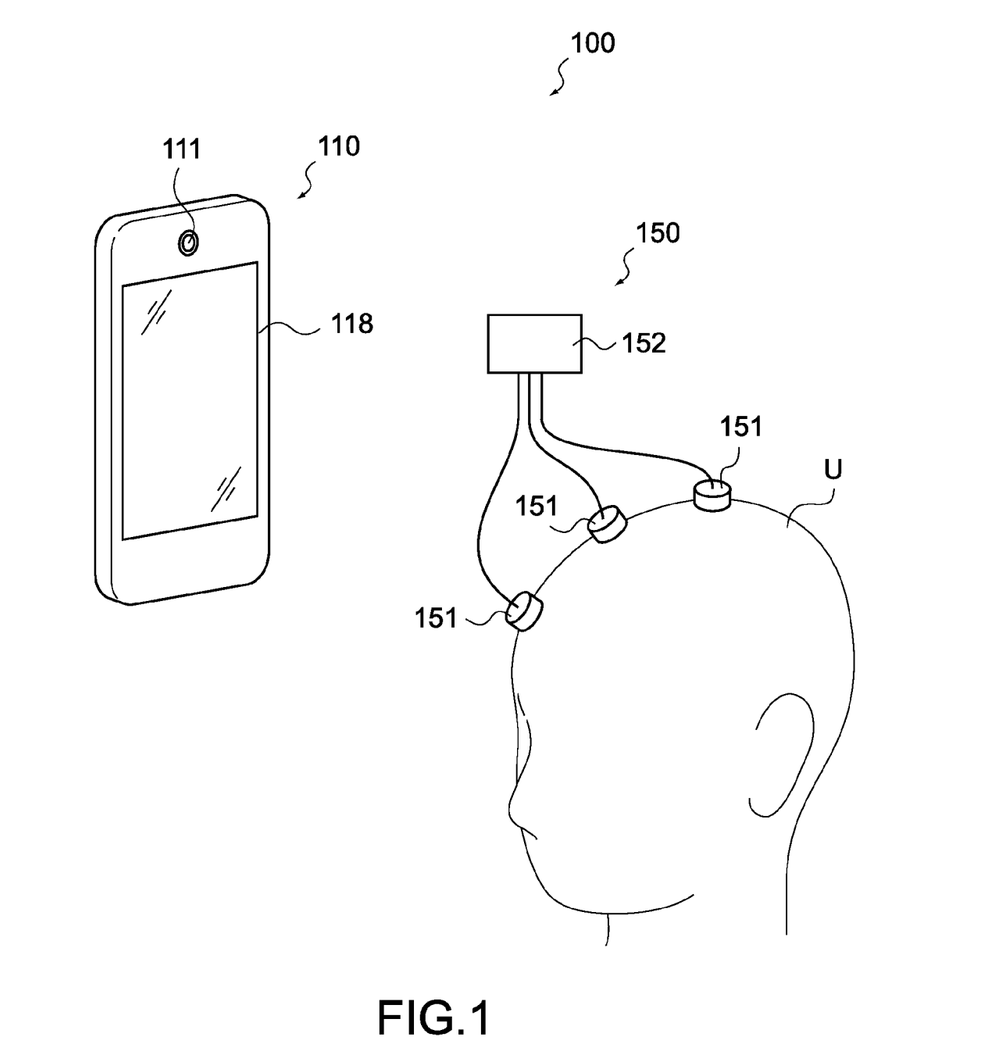
FIG. 1 is a schematic view showing a configuration of a biosignal measurement set according to an embodiment of the present disclosure.

FIG. 1 is a schematic view showing a configuration of a biosignal measurement set 100 according to this embodiment. As shown in the figure, the biosignal measurement set 100 includes an information processing apparatus 110 and a biosignal measurement apparatus 150.

The information processing apparatus 110 includes various information processing apparatuses such as a smart phone, a tablet personal computer (PC), and a desktop PC. The information processing apparatus 110 is not particularly limited. The biosignal measurement apparatus 150 is an apparatus that includes biosignal detection sensors 151 attached to the body of a user (user U in figure) and measures biosignals from the body of the user. Hereinafter, it is assumed that the biosignal measurement apparatus 150 is an electroencephalographic apparatus that measures brain waves of the user. However, the biosignal measurement apparatus 150 is not limited thereto. The biosignal measurement apparatus 150 may be an apparatus that measures various biosignals such as electrocardiogram, blood oxygen saturation level ($SpO_2$), and blood pressure.

The information processing apparatus 110 and the biosignal measurement apparatus 150 may be connected to each other by a wireless communication. Note that the information processing apparatus 110 and the biosignal measurement apparatus 150 may be connected to each other via a wire. The information processing apparatus 110 and the biosignal measurement apparatus 150 may also be connected to each other via another apparatus.

Figure 2:
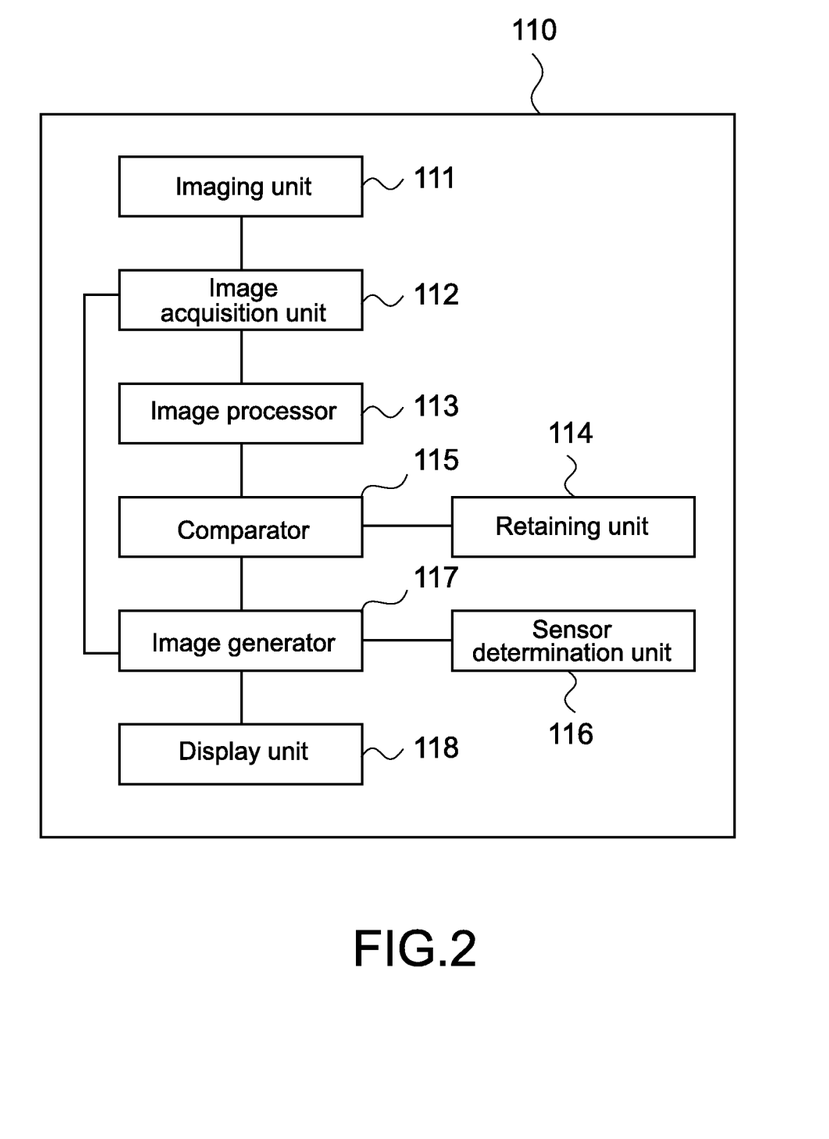
FIG. 2 is a schematic view showing a functional configuration of an information processing apparatus constituting the biosignal measurement set.

The information processing apparatus 110 includes a central processing unit (CPU) and a memory. A functional configuration as follows is realized in cooperation with a read-in program. FIG. 2 is a schematic view showing a functional configuration of the information processing apparatus 110. As shown in the figure, the information processing apparatus 110 includes an imaging unit 111, an image acquisition unit 112, an image processor 113, a retaining unit 114, a comparator 115, a sensor determination unit 116, an image generator 117, and a display unit 118.

The imaging unit 111 includes an optical system, an imaging element, and the like. The imaging unit 111 captures an image (including moving image) in the range of vision. One having a field of view in the same direction as the display unit 118 in the information processing apparatus 110 is favorably used as the imaging unit 111 (see FIG. 1). Alternatively, the imaging unit 111 may be configured independently of the information processing apparatus 110 and may be connected to the information processing apparatus 110 via a wiring or the like. The imaging unit 111 provides a captured image (hereinafter, referred to as capture image) to the image acquisition unit 112.

The image acquisition unit 112 acquires the capture image captured by the imaging unit 111. Note that the image acquisition unit 112 may acquire the capture image directly from the imaging unit 111 or may acquire the capture image via a network or the like. The image acquisition unit 112 provides the acquired capture image to the image processor 113 and the image generator 117.

The image processor 113 performs image processing on the capture image and extracts the body shape of the user included in the capture image. Extraction of the body shape can be performed by utilizing a well-known edge detection algorithm, facial recognition algorithm, or the like. The image processor 113 provides the extracted body shape of the user to the comparator 115. In addition, after the user attaches the biosignal detection sensors 151 to the body of the user, the image processor 113 may recognize the biosignal detection sensors 151 and detect positions thereof (hereinafter, referred to as detected attachment positions). The image processor 113 may recognize the biosignal detection sensors 151 by utilizing identification indicators provided to the biosignal detection sensors 151 in advance. In this case, the image processor 113 provides also the detected attachment positions to the comparator 115.

The retaining unit 114 retains attachment positions (hereinafter, referred to as defined attachment positions) of the biological detection sensors 151 with respect to the body site of the user, the attachment positions being defined in advance. In the case where the biosignal detection sensors 151 are electroencephalographic electrodes, the defined attachment positions are, for example, based on an electrode arrangement complying with the International 10-20 System. In addition to this, depending on the kind and measurement purpose of the biosignal detection sensors 151, the defined attachment positions can be appropriately set. The retaining unit 114 may retain the defined attachment positions in a storage or the like or may acquire the defined attachment positions via a network. The retaining unit 114 provides the retained defined attachment positions to the comparator 115.

The comparator 115 compares the body shape of the user extracted from the capture image by the image processor 113 with the defined attachment positions supplied from the retaining unit 114. Specifically, the comparator 115 compares the body shape of the user in the capture image with the body shape that is a reference for the defined attachment positions. The comparator 115 associates the defined attachment positions with the body shape of the user in the capture image. The comparator 115 provides that comparison result to the image generator 117. Further, when the comparator 115 is provided with the detected attachment positions from the image processor 113, the comparator 115 performs a comparison of the associated defined attachment positions and the detected attachment positions, and provides a comparison result to the image generator 117.

A sensor determination unit 116 determines attachment state of each of the biosignal detection sensors 151. Specifically, the attachment state means an attachment direction of the biosignal detection sensor 151, a degree of contact of the biosignal detection sensor 151 with a surface of a living body, and the like. The sensor determination unit 116 can acquire, for example, contact resistance between the biosignal detection sensor 151 and the surface of the living body from the biosignal measurement apparatus 150. When the contact between the biosignal detection sensor 151 and the surface of the living body is insufficient, the contact resistance significantly increases. Therefore, the sensor determination unit 116 can determine, based on the contact resistance, the attachment state of the biosignal detection sensor 151. Other than the contact resistance, the sensor determination unit 116 can determine, based on information indicating the attachment state of the biosignal detection sensor 151, the attachment state of the biosignal detection sensor 151. The sensor determination unit 116 provides a determination result to the image generator 117.

The image generator 117 generates, based on the comparison result by the comparator 115, an image to be displayed by the display unit 118 (hereinafter, referred to as display image). Specifically, the image generator 117 may generate the display image by overlapping a marker on the capture image provided from the image acquisition unit 112. The marker is located at the defined attachment position (comparison result) associated with the body shape of the user in the capture image. With this, an image in which the marker is located at a position corresponding to the defined attachment position in a picture of the user within the capture image is generated as the display image.

Further, when the image generator 117 is provided with the comparison result of the defined attachment position and the detected attachment position from the comparator 115, the image generator 117 may generate the display image based on that comparison result. Specifically, when the defined attachment position is different from the detected attachment position, that is, when the biosignal detection sensor 151 attached by the user is not attached at the defined attachment position, the image generator 117 may locate the marker at a position (normal attachment position) on the capture image, the position corresponding to the defined attachment position.

In addition, when the image generator 117 is provided with a determination result of the attachment state of the biosignal detection sensor 151 from the sensor determination unit 116, the image generator 117 may generate the display image based on the attachment state. Specifically, the image generator 117 may locate the marker at a position (normal attachment position) on the capture image, the position corresponding to the defined attachment position of the biosignal detection sensor 151 the attachment state of which is inappropriate. The image generator 117 provides the generated display image to the display unit 118.

The display unit 118 includes an image display element and the like and displays the display image provided from the image generator 117. Further, the display unit 118 may be configured independently of the information processing apparatus 110 and may display the display image provided via a wire or the like.

The information processing apparatus 110 has the above-mentioned configuration.

The biosignal measurement apparatus 150 includes the biosignal detection sensors 151 and a control unit 152. The number of biosignal detection sensors 151 may be one or more. Each of the biosignal detection sensors 151 is connected to the control unit 152 in a wired or wireless manner.

The biosignal detection sensors 151 are attached to the body of the user and detect biosignals of the user. The biosignals may be any of various signals indicating states of a living body such as brain waves, electrocardiogram, electromyogram, blood oxygen saturation level ($SpO_2$), and blood pressure. Each of the biosignal detection sensors 151 only needs to be capable of detecting a biosignal being a measurement target and attached to the body of the user. For example, the biosignal detection sensor 151 may be a brain wave detection electrode. The biosignal detection sensor 151 provides the detected biosignal to the control unit 152. Further, the biosignal detection sensor 151 may be provided with an identification indicator (e.g., light emitting unit) to be utilized by the image processor 113 to recognize the biosignal detection sensor 151.

The control unit 152 includes a signal processing circuit and the like and processes outputs of the biosignal detection sensors 151. Alternatively, the control unit 152 may include a wireless communication module and transmit the outputs of the biosignal detection sensors 151 (including output processing results) to the information processing apparatus 110.

The biosignal measurement apparatus 150 has the above-mentioned configuration. Note that the biosignal measurement apparatus 150 may include equipment for attaching the biosignal detection sensors 151 to the body of the user.

[Operation of Biosignal Measurement Set]

An operation of the biosignal measurement set 100 will be described.

Figure 3:
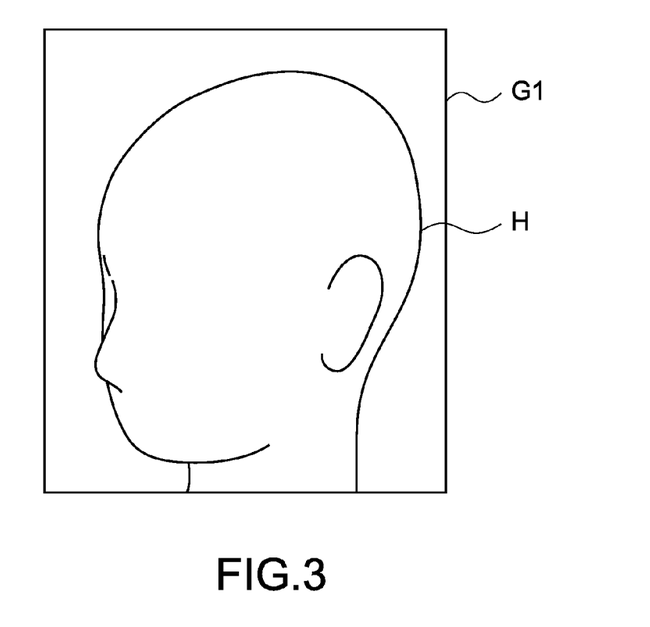
FIG. 3 is an example of a capture image captured by an imaging unit of the information processing apparatus constituting the biosignal measurement set.

The user directs the imaging unit 111 of the information processing apparatus 110 to the user. Capturing of the capture image is started. Although capturing of the capture image may be continuously performed, that is, the capture images may constitute a moving image, one capture image will be described as an example in the following description. FIG. 3 shows a capture image G1 as an example of the capture image.

The image acquisition unit 112 acquires the capture image G1 from the imaging unit 111 and provides the capture image G1 to the image processor 113 and the image generator 117.

Figure 4:
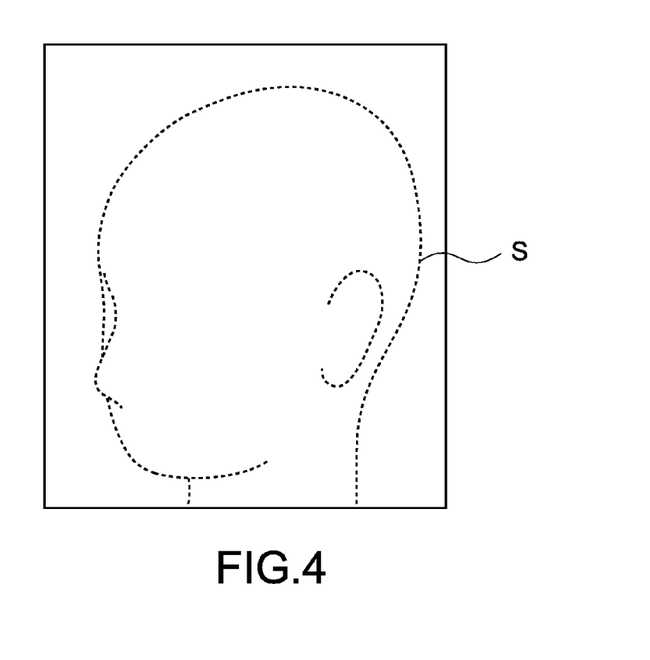
FIG. 4 is a schematic view showing a body shape of a user that is extracted by an image processor of the information processing apparatus constituting the biosignal measurement set.

The image processor 113 extracts the body shape of the user from the capture image G1. FIG. 4 is a schematic view showing a body shape S of the user extracted by the image processor 113. The image processor 113 provides the extracted body shape S to the comparator 115.

Figure 5:
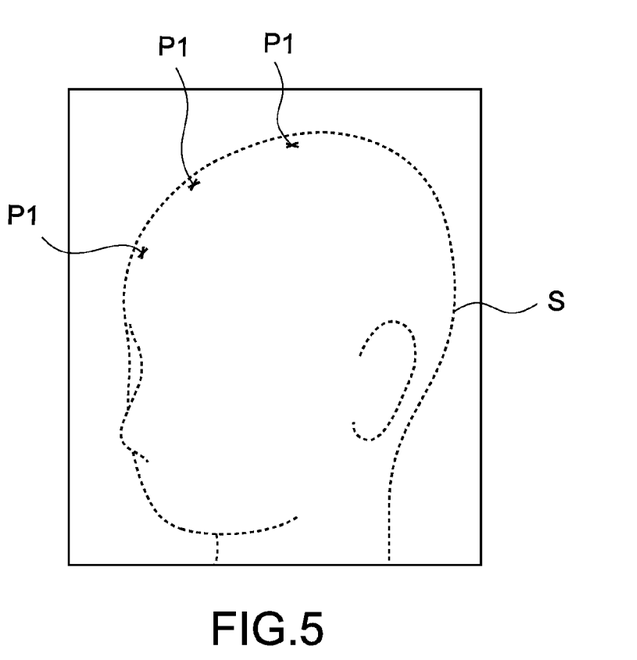
FIG. 5 is a schematic view showing a defined attachment position associated with the body shape by a comparator of the information processing apparatus constituting the biosignal measurement set.

The comparator 115 compares the body shape S with the defined attachment position provided from the retaining unit 114. The comparator 115 associates the body shape S and the defined attachment position with each other. FIG. 5 shows defined attachment positions P1 associated with the body shape S by the comparator 115. The comparator 115 provides a comparison result thereof to the image generator 117.

Figure 6:
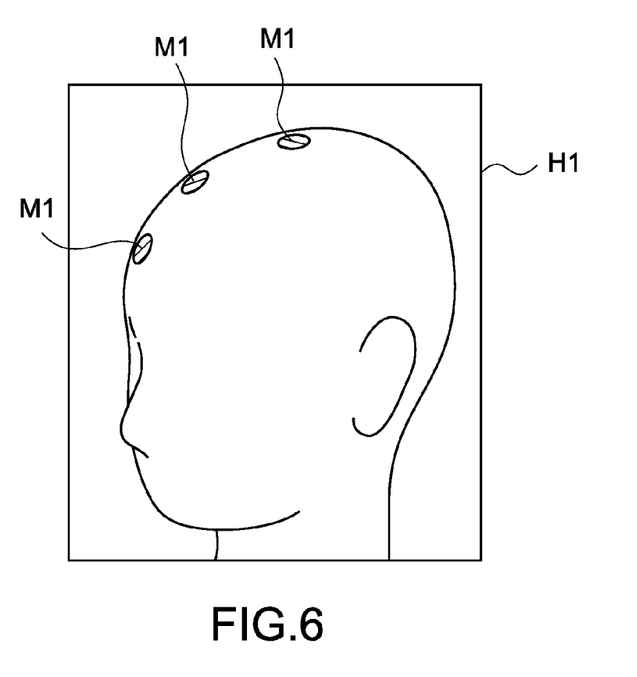
FIG. 6 is an example of a display image generated by the image generator of the information processing apparatus constituting the biosignal measurement set.

The image generator 117 locates markers at the defined attachment positions P1 on the capture image G1 and generates the display image. FIG. 6 shows a display image H1 generated by the image generator 117. The markers located at the defined attachment positions P1 in the display image H1 are shown as markers M1. The image generator 117 provides the display image H1 to the display unit 118.

The display unit 118 displays the display image H1. With this, the user is allowed to check a position at which the biosignal detection sensor 151 is to be attached in the display image H1. As mentioned above, the markers M1 are located based on the body shape S of the user extracted from the capture image G1, and hence the positions are adjusted depending on an individual difference of the body shape of the user. Further, even if the user moves the body or the imaging unit 111 in capturing the capture image G1, the above-mentioned process is performed on the newly captured capture image G1 and the display image H1 is generated. Therefore, the markers M1 move following the body shape of the user. Therefore, referring to the display image H1, the user can accurately grasp a position at which the biosignal detection sensor 151 is to be attached.

Figure 7:
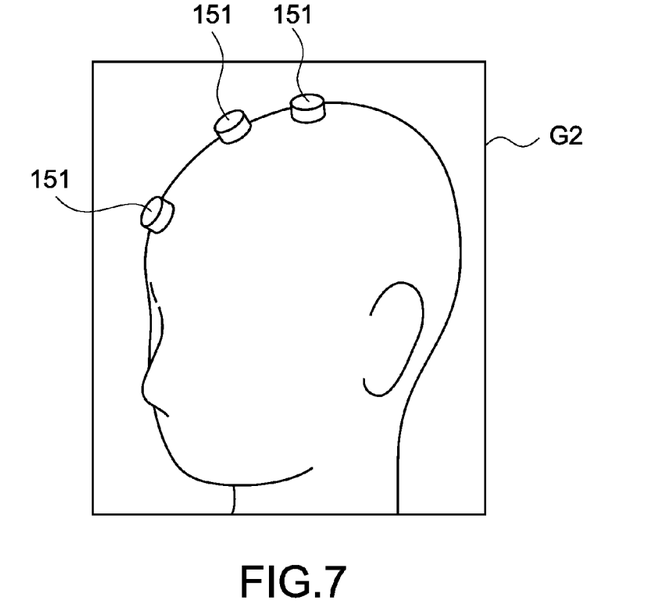
FIG. 7 is an example of a capture image captured by an imaging unit of the information processing apparatus constituting the biosignal measurement set.

Subsequently, it is assumed that the user attaches the biosignal detection sensor 151 to the user, referring to the display image H1. FIG. 7 shows a capture image G2 captured by the imaging unit 111.

Figure 8:
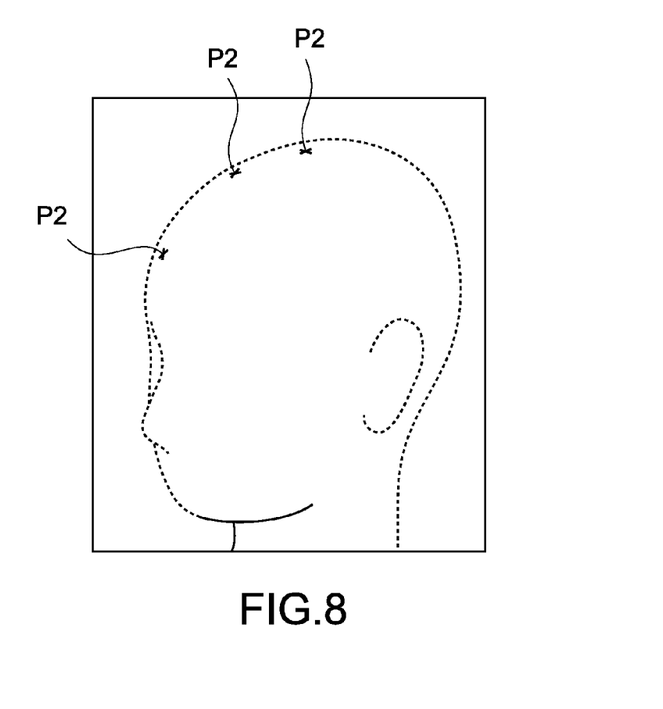
FIG. 8 is a schematic view showing a detected attachment position detected by an image processor of the information processing apparatus constituting the biosignal measurement set.

The image processor 113 detects the detected attachment position being the attachment position of the biosignal detection sensor 151 together with the body shape of the user in the capture image G2. FIG. 8 shows detected attachment positions P2 detected by the image processor 113. The image processor 113 provides the detected attachment positions P2 to the comparator 115.

Figure 9:
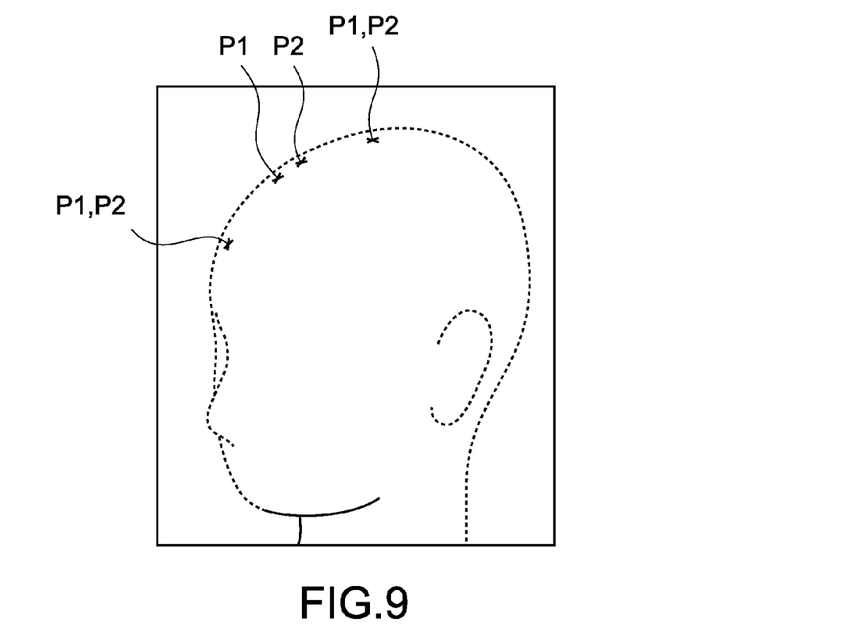
FIG. 9 is a schematic view showing the defined attachment position and the detected attachment position compared by the comparator of the information processing apparatus constituting the biosignal measurement set.

The comparator 115 compares the defined attachment positions P1 with the detected attachment positions P2. FIG. 9 shows the defined attachment positions P1 and the detected attachment positions P2. As shown in the figure, when one of the detected attachment positions P2 is different from the defined attachment position P1, that is, if the position of one of the biosignal detection sensors 151 is different from an appropriate attachment position, the comparator 115 provides that difference to the image generator 117 as a comparison result.

Figure 10:
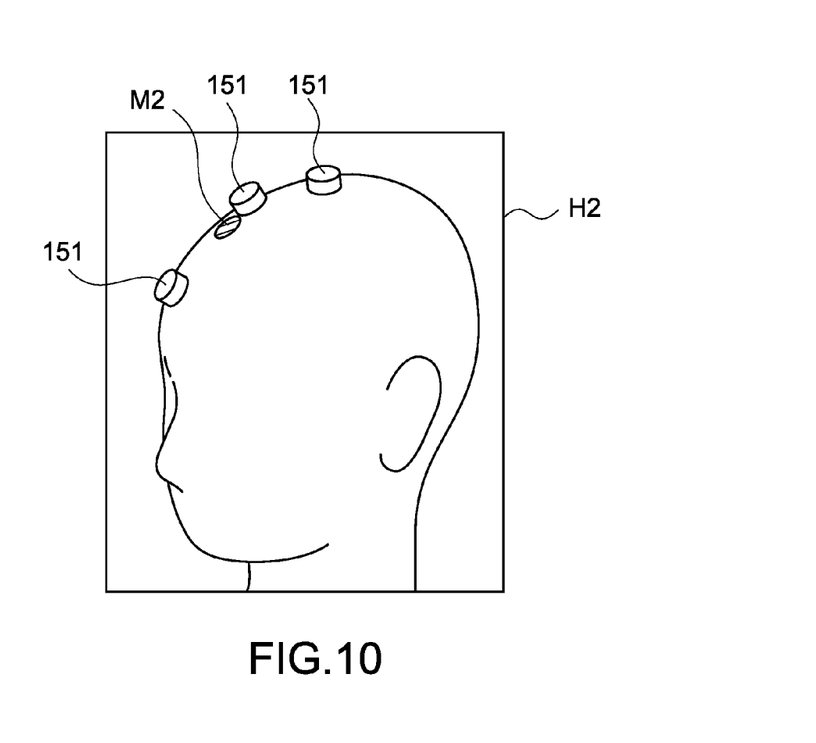
FIG. 10 is an example of the display image generated by the image generator of the information processing apparatus constituting the biosignal measurement set.

When the image generator 117 is provided with the difference between the detected attachment position P2 and the defined attachment position P1 from the comparator 115, the image generator 117 generates a display image by locating a marker at the defined attachment position P1 on the capture image G2, at which the difference occurs. FIG. 10 shows a display image H2 generated by the image generator 117. The marker located at the defined attachment position P1 in the display image H2, at which the difference occurs, is shown as a marker M2. The image generator 117 may warn the user by blinking the marker M2 or by changing a color, for example. Further, the image generator 117 may also display the markers M1 in the display image H2. The image generator 117 provides the display image H2 to the display unit 118.

The display unit 118 displays the display image H2. With this, the user can check that the biosignal detection sensor 151 is attached at a position different from a position at which the biosignal detection sensor 151 is to be normally attached.

Further, after the user attaches the biosignal detection sensor 151 to him or her, the sensor determination unit 116 determines the attachment state of the biosignal detection sensor 151. Specifically, the sensor determination unit 116 may acquire, from the control unit 152 of the biosignal measurement apparatus 150, an output (contact resistance, etc.) of the biosignal detection sensor 151. Based on the acquired output, the sensor determination unit 116 determines whether or not the attachment state of the biosignal detection sensor 151 is appropriate. The sensor determination unit 116 provides a determination result to the image generator 117.

Figure 11:
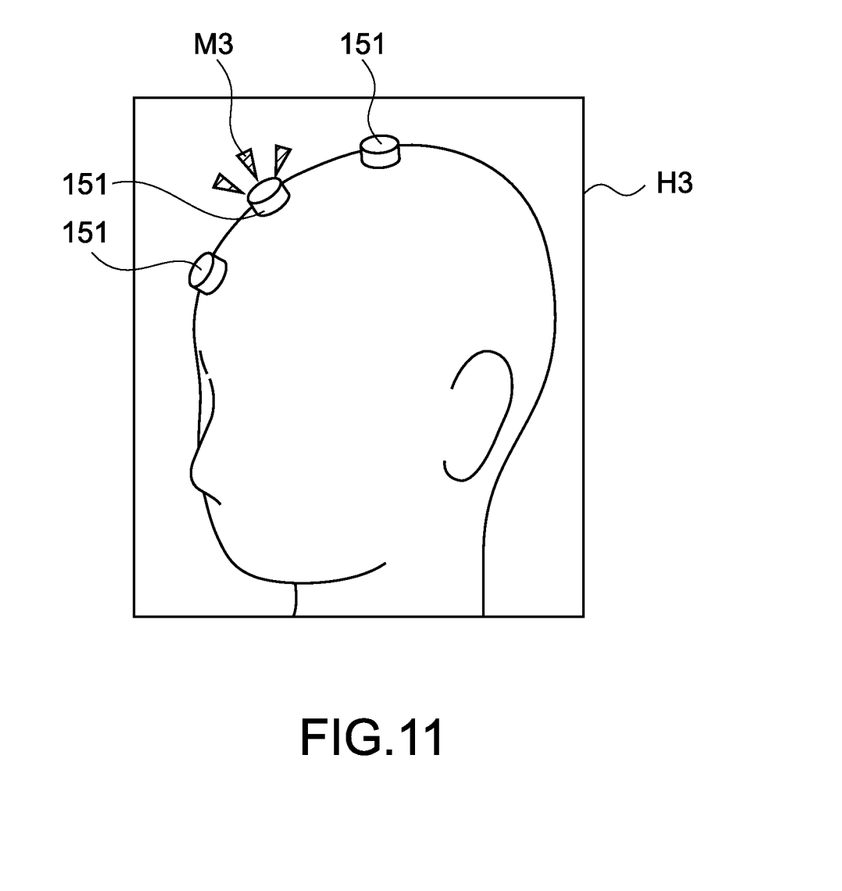
FIG. 11 is an example of the display image generated by the image generator of the information processing apparatus constituting the biosignal measurement set.

When the image generator 117 is provided with a determination result from the sensor determination unit 116, the image generator 117 generates the display image by locating the marker at the defined attachment position of the biosignal detection sensor 151 the attachment state of which is inappropriate, or in vicinity thereof. FIG. 11 shows a display image H3 generated by the image generator 117. In the display image H3, the marker located in vicinity of the biosignal detection sensor 151 the attachment state of which is inappropriate is shown as a marker M3. The image generator 117 may warn the user by blinking the marker M3 or changing a color, for example. Further, the image generator 117 may display also the markers M1 in the display image H3 and may present, to the user, the fact that the attachment state is appropriate by changing a color, for example. The image generator 117 provides the display image H3 to the display unit 118.

The display unit 118 displays the display image H3. With this, the user can check whether or not the attachment state of the biosignal detection sensor 151 is appropriate.

As mentioned above, with the biosignal measurement set 100 according to this embodiment, the user can easily grasp a position at which the biosignal detection sensor 151 is to be attached. Further, also after the biosignal detection sensor 151 is attached, it is possible to grasp a difference of the attachment position or appropriateness or inappropriateness of the attachment state. It becomes possible to accurately measure a biosignal.

The present disclosure is not limited only to the above-mentioned embodiment and may be changed without departing from the gist of the present disclosure.

In the above-mentioned embodiment, the information processing apparatus displays the marker at the attachment position of the biological detection sensor. However, the information processing apparatus may display an attachment method for the biological detection sensor together with the marker. Alternatively, the information processing apparatus may present the attachment position of the biological detection sensor to the user by displaying the marker with sound.

Further, in the above-mentioned embodiment, by recording the capture image captured by the imaging unit, another person (doctor, etc.) can thereafter check the attachment state of the biological detection sensor of the user. With this, if a measurement result is abnormal, for example, that person can utilize the capture image for determining a reason for this. Alternatively, the capture image may be provided to that person via a network at real time.

It should be noted that the present disclosure may also take the following configurations.

(1) An information processing apparatus, including:
a retaining unit configured to retain a defined attachment position being an attachment position of a biological detection sensor with respect to a body site of a user, the defined attachment position being defined in advance;
an image acquisition unit configured to acquire a capture image captured by an imaging unit;
an image processor configured to extract, from the capture image, a body shape of the user;
a comparator configured to compare the body shape with the defined attachment position; and
an image generator configured to generate, based on a comparison result by the comparator, a display image to be displayed on a display unit.

(2) The information processing apparatus according to Item (1), in which
the image generator is configured to generate the display image by overlapping the capture image with a marker located at a position on the capture image, the position corresponding to the defined attachment position. (3) The information processing apparatus according to Item (1) or (2), in which
the image processor is configured to further detect, from the capture image, a detected attachment position being an attachment position of a biological detection sensor, and
the comparator is configured to further compare the defined attachment position with the detected attachment position.

(4) The information processing apparatus according to any one of Items (1) to (3), in which
the image generator is configured to generate, when the defined attachment position is different from the detected attachment position, the display image by overlapping the capture image with a marker located at a position on the capture image, the position corresponding to the defined attachment position different from the detected attachment position.

(5) The information processing apparatus according to any one of Items (1) to (4), further including
a sensor determination unit configured to determine an attachment state of the biological detection sensor, in which
the image generator is configured to further generate the display image based on a determination result of the sensor determination unit.

(6) The information processing apparatus according to any one of Items (1) to (5), in which
the image generator is configured to generate, when the attachment state is inappropriate, the display image by overlapping the capture image with a marker located at a position on the capture image, the position corresponding to the defined attachment position of the biological detection sensor the attachment state of which is inappropriate.

(7) The information processing apparatus according to any one of Items (1) to (6), in which
the biological detection sensor includes an electroencephalographic electrode, and
the sensor determination unit is configured to determine the attachment state based on contact resistance of the electroencephalographic electrode.

(8) A program that causes an information processing apparatus to function as:
a retaining unit configured to retain a defined attachment position being an attachment position of a biological detection sensor with respect to a body site of a user, the defined attachment position being defined in advance;

an image acquisition unit configured to acquire a capture image captured by an imaging unit;

an image processor configured to extract, from the capture image, a body shape of the user;

a comparator configured to compare the body shape with the defined attachment position; and an image generator configured to generate, based on a comparison result by the comparator, a display image to be displayed on a display unit.

(9) A biosignal measurement set, including:

a biosignal measurement apparatus including a biological detection sensor configured to detect a biosignal in a body of a user; and an information processing apparatus including a retaining unit configured to retain a defined attachment position being an attachment position of the biological detection sensor to a body site of a user, the defined attachment position being defined in advance, an image acquisition unit configured to acquire a capture image captured by an imaging unit, an image processor configured to extract, from the capture image, a body shape of the user, a comparator configured to compare the body shape with the defined attachment position, and an image generator configured to generate, based on a comparison result by the comparator, a display image to be displayed on a display unit.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An information processing apparatus, comprising:
a retaining unit configured to retain a defined attachment position being an attachment position of a biological detection sensor with respect to a body site of a user;
an image acquisition unit configured to acquire an image;
an image processor configured to extract, from the image, a body shape of the user;
a comparator configured to compare the body shape with the defined attachment position; and
an image generator configured to generate, based on a comparison result by the comparator and an attachment state of the biological detection sensor with respect to the body site, a display image to be displayed on a display unit,
wherein the attachment state indicates a degree of contact of the biological detection sensor with a surface of the body site.

2. The information processing apparatus according to claim 1, wherein
the image generator, to generate the display image, is further configured to overlap the image with a marker located at a position on the image, the position corresponding to the defined attachment position.

3. The information processing apparatus according to claim 1,
wherein the image processor is further configured to detect, from the image, a detected attachment position being an attachment position of the biological detection sensor, and the comparator is further configured to compare the defined attachment position with the detected attachment position.

4. The information processing apparatus according to claim 3,
wherein the image generator, to generate the display image and based on a determination that the defined attachment position is different from the detected attachment position, is further configured to overlap the image with a marker located at a position on the image, the position corresponding to the defined attachment position different from the detected attachment position.

5. The information processing apparatus according to claim 1, further comprising:
a sensor determination unit configured to determine the attachment state of the biological detection sensor.

6. The information processing apparatus according to claim 5,
wherein the image generator, to generate the display image and based on a determination that the attachment state is inappropriate, is further configured to overlap the image with a marker located at a position on the image, the position corresponding to the defined attachment position of the biological detection sensor the attachment state of which is inappropriate.

7. The information processing apparatus according to claim 5,
wherein the biological detection sensor includes an electroencephalographic electrode, and
the sensor determination unit is further configured to determine the attachment state based on contact resistance of the electroencephalographic electrode.

8. The information processing apparatus according to claim 1, wherein the attachment state further indicates an attachment direction of the biological detection sensor with respect to the body site.

9. The information processing apparatus according to claim 1, the defined attachment position is defined in advance.

10. A non-transitory computer-readable storage medium having stored thereon, a set of computer-executable instructions for causing an information processing apparatus to execute operations, comprising:
retaining a defined attachment position being an attachment position of a biological detection sensor with respect to a body site of a user;
acquiring an image;
extracting, from the image, a body shape of the user;
comparing the body shape with the defined attachment position; and
generating, based on a comparison result and an attachment state of the biological detection sensor with respect to the body site, a display image to be displayed,
wherein the attachment state indicates a degree of contact of the biological detection sensor with a surface of the body site.

11. A biosignal measurement system, comprising:
a biological measurement apparatus which includes a biological detection sensor configured to detect a biosignal in a body of a user; and
an information processing apparatus which includes:
a retaining unit configured to retain a defined attachment position being an attachment position of the biological detection sensor with respect to a body site of a user, an image acquisition unit configured to acquire an image,
an image processor configured to extract, from the image, a body shape of the user,
a comparator configured to compare the body shape with the defined attachment position, and
an image generator configured to generate, based on a comparison result by the comparator and an attachment state of the biological detection sensor with respect to the body site, a display image to be displayed on a display unit,
wherein the attachment state indicates a degree of contact of the biological detection sensor with a surface of the body site.

* * * * *